United States Patent
Wilson et al.

(10) Patent No.: US 9,114,230 B2
(45) Date of Patent: Aug. 25, 2015

(54) VALVE SYSTEM AND METHOD WITH MULTI-DIRECTIONAL PUMPING

(71) Applicant: DEPUY SYNTHES PRODUCTS, LLC, Raynham, MA (US)

(72) Inventors: Stephen Wilson, N. Easton, MA (US); Brian Soares, Norton, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 13/629,661

(22) Filed: Sep. 28, 2012

(65) Prior Publication Data
US 2014/0094735 A1    Apr. 3, 2014

(51) Int. Cl.
*A61M 27/00* (2006.01)
*A61M 5/142* (2006.01)

(52) U.S. Cl.
CPC .......... *A61M 27/006* (2013.01); *A61M 5/1428* (2013.01)

(58) Field of Classification Search
CPC .............. A61M 27/00; A61M 27/006; A61M 2027/004; A61M 5/1428
USPC ........................................................ 604/8, 9
See application file for complete search history.

(56) References Cited

U.S. PATENT DOCUMENTS

| | | | |
|---|---|---|---|
| 3,503,402 A | 3/1970 | Schulte | |
| 3,827,439 A | 8/1974 | Schulte | |
| 4,464,168 A * | 8/1984 | Redmond et al. | 604/9 |
| 4,552,553 A | 11/1985 | Schulte | |
| 4,560,375 A | 12/1985 | Schulte | |
| 4,636,194 A | 1/1987 | Schulte | |
| 5,154,693 A | 10/1992 | East | |
| 5,167,615 A | 12/1992 | East | |
| 5,176,627 A | 1/1993 | Watson | |
| 5,584,314 A | 12/1996 | Bron | |
| 5,637,083 A | 6/1997 | Bertrand | |
| 7,094,214 B2 | 8/2006 | Dextradeur | |
| 2008/0281250 A1 | 11/2008 | Bergsneider | |
| 2009/0277850 A1 | 11/2009 | Adams | |
| 2010/0121250 A1 * | 5/2010 | Pizzi | 604/10 |
| 2011/0060265 A1 | 3/2011 | Dragoon | |
| 2012/0046595 A1 | 2/2012 | Wilson | |

FOREIGN PATENT DOCUMENTS

| | | |
|---|---|---|
| EP | 068815 A1 | 1/1983 |
| FR | 2569987 A1 | 3/1986 |
| WO | WO 2007092875 | 8/2007 |

OTHER PUBLICATIONS

European Search Report EP13186472.0 dated Dec. 5, 2013.

* cited by examiner

*Primary Examiner* — Philip R Wiest
*Assistant Examiner* — Benjamin Klein

(57) ABSTRACT

An implantable valve system and method of using same, including a housing with a resilient membrane defining a reservoir in fluid communication with at least two ports, and at least a first set of opposing sealing features disposed on upper and lower surfaces within the housing. The membrane is capable of being depressed by a human finger to bring the sealing features together to substantially restrict fluid from passing through at least one of one of the ports, and is capable of being depressed additionally by a rolling motion of the finger to drive fluid through the other of the ports.

6 Claims, 2 Drawing Sheets

VALVE SYSTEM AND METHOD WITH MULTI-DIRECTIONAL PUMPING

BACKGROUND OF THE INVENTION

1. Field of the Invention

The invention relates to clearing obstructions from implanted catheters and more particularly to a hydrocephalus valve which can be manually pumped to flush attached catheters.

2. Description of the Related Art

There are a number of treatments for medical conditions which require fluid to be removed from an organ or tissue of a patient. One such condition is hydrocephalus, where cerebrospinal fluid abnormally accumulates in the skull faster than it is withdrawn by the body. The excessive build-up of cerebrospinal fluid compresses brain tissues, which eventually leads to brain damage.

Hydrocephalus is commonly treated by implanting a shunt system, typically including a ventricular catheter in fluid communication with a ventricle within the brain, to withdraw cerebrospinal fluid at a desired rate. The rate of withdrawal of cerebrospinal fluid is usually controlled by a valve, located in a housing disposed between the ventricular catheter and a drainage catheter, having one or more pressure settings.

Complications due to obstructions within the shunt system are detailed in U.S. Pat. No. 7,094,214 by Dextradeur et al., for example. That patent discloses a multi-electrode system for clearing obstructions in a blocked catheter after a probe is inserted into a socket to energize the electrodes.

Other systems utilize a multiple finger approach whereby one finger closes a valve or blocks a catheter while a second finger pushes on the housing to pump cerebrospinal fluid from a reservoir into the blocked catheter, such as shown in U.S. Pat. No. 4,560,375 by Schulte et al. Many systems may be suited for clearing a blockage in one direction but are less suited for clearing blockages in the opposite direction.

It is therefore desirable to have an implantable valve system which enables both proximal and distal implanted catheters to be easily cleared of obstructions.

SUMMARY OF THE INVENTION

An object of the present invention is to provide an improved valve system which can be easily operated to clear an obstruction utilizing a single finger.

Another object of the present invention is to provide such a valve system which is capable of multi-directional pumping.

This invention results from the realization that an improved valve system can be manipulated utilizing a single finger to close at least a first set of opposing sealing features. The same finger is then rolled to pump fluid in a desired direction.

This invention features an implantable valve system and method of using same, including a housing with a resilient membrane defining a reservoir in fluid communication with at least two ports and having a longitudinal axis, and at least a first set of opposing sealing features disposed on upper and lower surfaces within the housing. The membrane is capable of being depressed by a human finger to bring the sealing features together to substantially restrict fluid from passing through at least one of one of the ports, and is capable of being depressed additionally by a rolling motion of the finger to drive fluid through the other of the ports.

In some embodiments, the first set of opposing sealing features is disposed transverse to the longitudinal axis of the housing. In one embodiment, the first set of opposing sealing features extends substantially perpendicularly across the reservoir to establish first and second pumping chambers when the sealing features are brought together.

In certain embodiments, one of the sealing features includes a detent and the other of the sealing features includes a recess to matingly receive the detent. In some embodiments, the housing further includes a floor portion which defines one of the sealing features.

In other embodiments, the valve system includes at least a second set of sealing features capable of substantially restricting fluid from passing through the other of the ports when the membrane is depressed in the vicinity of the second set. In some embodiments, the first set and the second set are longitudinally spaced from each other.

This invention also features a method for clearing an obstruction in one or more catheters implanted in a patient by locating a valve system implanted sub-dermally in the patient, the valve system having a housing with a resilient membrane defining a reservoir in fluid communication with at least two ports and having at least a first set of opposing sealing features disposed on upper and lower surfaces within the housing. The membrane is depressed with one finger to bring the sealing features together to substantially restrict fluid from passing through at least one of one of the ports. The finger is then moved in a rolling motion to additionally depress the membrane to drive fluid through the other of the ports to clear the obstruction.

The method may further include moving the finger in a second rolling motion in a second direction to additionally depress the membrane to drive fluid in the second direction through the one of the ports to clear a second obstruction. In some embodiments, the valve system includes at least a second set of sealing features and the method further includes, prior to moving the finger in the second rolling motion, lifting the finger after the first rolling motion and depressing the membrane with the finger to bring the second set of sealing features together.

BRIEF DESCRIPTION OF THE DRAWINGS

In what follows, preferred embodiments of the invention are explained in more detail with reference to the drawings, in which.

DETAILED DESCRIPTION OF THE PRESENTLY PREFERRED EMBODIMENTS

This invention may be accomplished by an implantable valve system and method of using same, including a housing with a resilient membrane defining a reservoir in fluid communication with at least two ports and having a longitudinal axis, and at least a first set of opposing sealing features disposed on upper and lower surfaces within the housing. The membrane is capable of being depressed by a human finger to bring the sealing features together to substantially restrict fluid from passing through at least one of one of the ports, and is capable of being depressed additionally by a rolling motion of the finger to drive fluid through the other of the ports.

Figure 1:
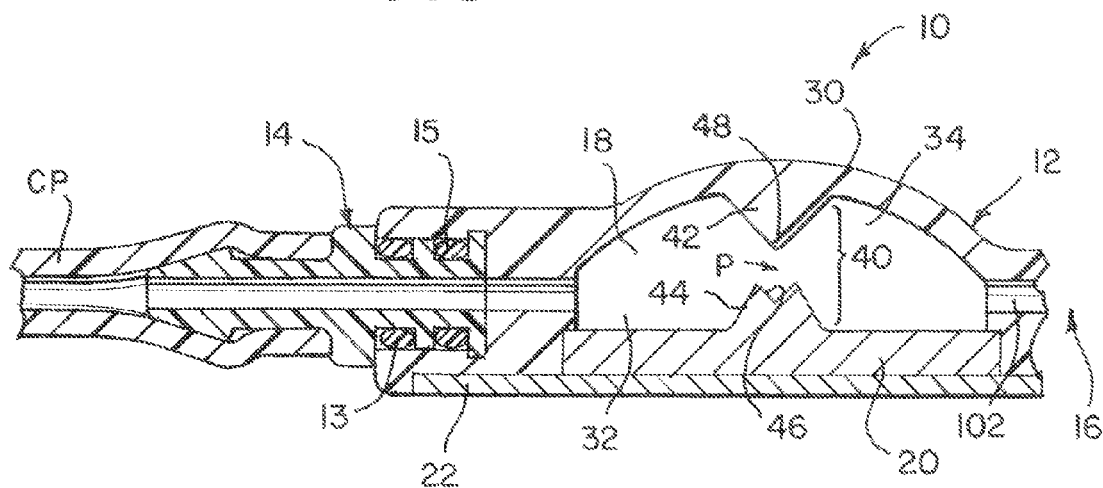
FIG. 1 is a schematic longitudinal cross-sectional side view of a valve system according to the present invention.
Figure 2:
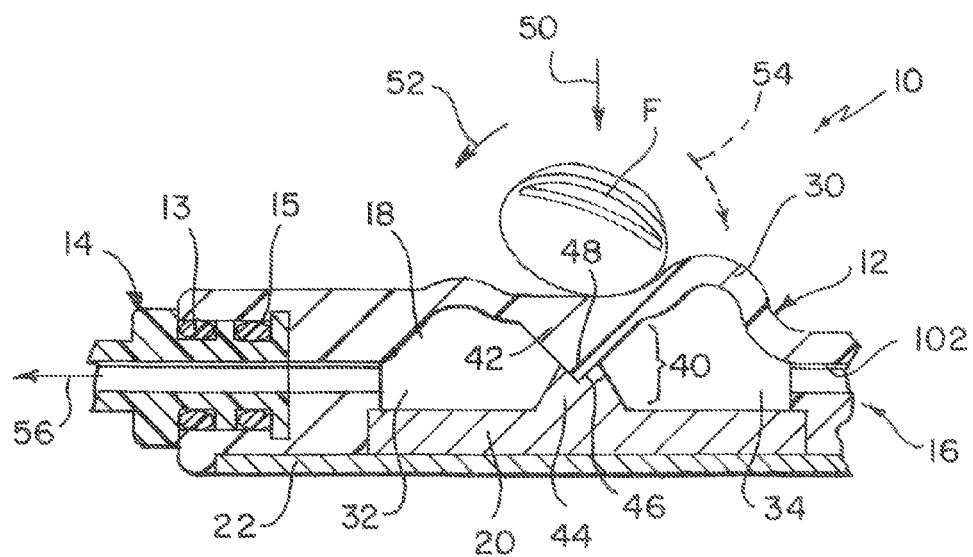
FIG. 2 is a view similar to FIG. 1 showing a single finger operating the valve system to clear an obstruction.

A shunt valve system 10 is shown in axial or longitudinal side cross-section in FIGS. 1 and 2 having a shunt housing 12 and a proximal connector 14, also referred to as a proximal port 14, with epoxy seals 13 and 15, shown connected to a proximal catheter CP, FIG. 1, such as a ventricular catheter, to normally bring fluid into housing 12. A distal port including a connector 16 connected to a distal catheter CD are not illustrated for purposes of drawing clarity. Also not illustrated are various other components such as a magnetically controllable valve unit 100 that are known to those skilled in the art, such as disclosed in U.S. Patent Publication 2012/0046595 by Wilson et al., which is incorporated herein in its entirety.

In this construction according to the present invention, a single set 40 of opposing features 42 and 44 are normally separated from each other to form a passage P within a reservoir 18 having pumping chambers 32 and 34. Feature 44 defines a recess or groove 46 to matingly receive detent or projecting ridge 48 of feature 42. Features 42 and 44 extend away and toward the viewer of FIGS. 1 and 2 such that pressure applied by finger F in the direction of arrow 50, FIG. 2, brings features 42 and 44 together to substantially restrict fluid flow there-between and to isolate chambers 32 and 34 from each other.

Housing 12 is formed of a resilient, preferably translucent, material such as silicone, at least in the region of membrane 30 to define the reservoir 18 with pumping chambers 32 and 34. Under normal conditions, FIG. 1, fluid passes into pumping chamber 32, flows through set 40 into pumping chamber 34, and then through a valve mechanism (not shown) in inlet 102.

Feature 44 is formed on a plate 20 and is elastomeric in some constructions and substantially rigid in other constructions. Preferably, at least one of plate 20 and backing plate 20 serve as a needle guard so that needles can be inserted into reservoir 18 to sample fluids or inject liquids for medical treatment or other purposes. Plate 20 and backing plate 22 form the floor of reservoir chamber 18 in this construction.

One method according to the present invention for clearing an obstruction in one or more catheters implanted in a patient includes locating the valve system 10 by palpating the region where valve system 10 is implanted sub-dermally in the patient. The membrane 18 is depressed with one finger F, FIG. 2, in the direction of arrow 50 to bring the sealing features 42 and 44 together to substantially restrict fluid from passing through at least port 16. The finger is then moved in a rolling motion, in the direction of arrow 52, to additionally depress the membrane 30 which compresses chamber 32 to drive fluid through the other of the port 14, as illustrated by arrow 56, to clear the obstruction in proximal catheter CP.

An obstruction in distal catheter CD can be cleared independently by instead moving the finger in a second rolling motion in a second direction, shown by dashed arrow 54, to additionally depress the membrane to drive fluid in the second direction through the valve inlet 102 and port 16 to clear the obstruction in catheter CD.

Figure 3:
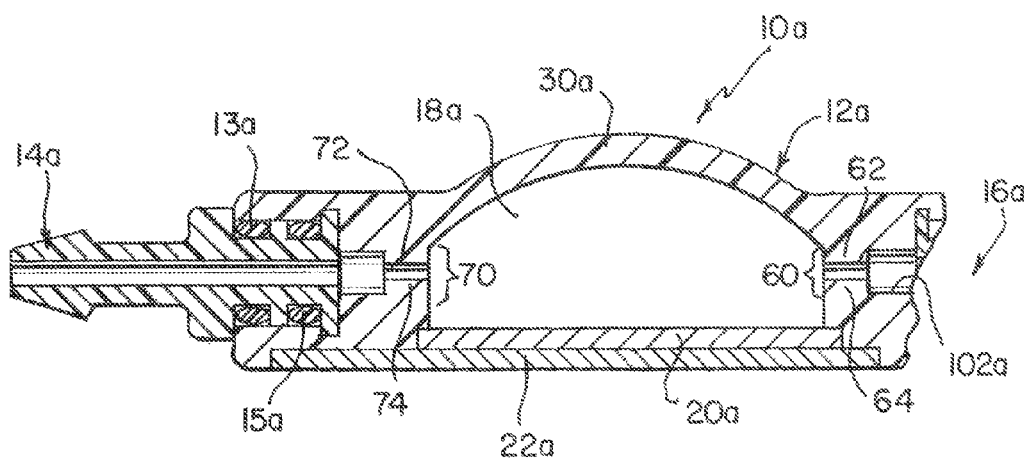
FIG. 3 is a schematic longitudinal cross-sectional side view of another valve system according to the present invention.
Figure 4:
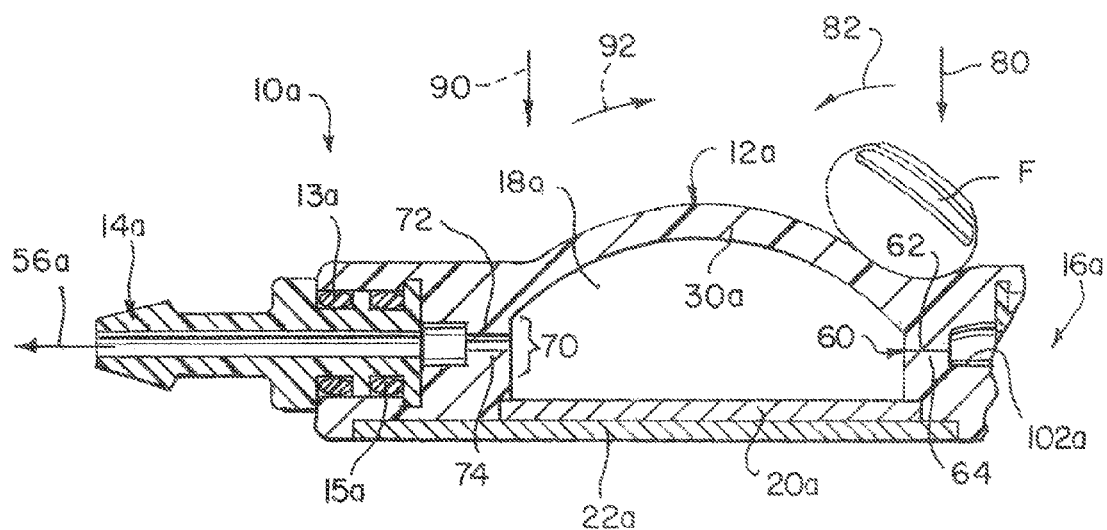
FIG. 4 is a view similar to FIG. 3 showing a single finger operating the valve system to clear an obstruction.

An alternative valve system 10a according to the present invention is schematically illustrated in longitudinal cross-section in FIGS. 3 and 4. Components that are similar to those of valve system 10, FIGS. 1 and 2, are numbered in a similar manner in FIGS. 3-4. In this construction, valve system 10a defines a unitary reservoir 18a and includes a first set 60 of opposing features 62 and 64 and a second set 70 of opposing features 72 and 74. A needle guard 20a, preferably formed of a rigid polymeric material, is secured within housing 12a by a backing plate 22a, preferably formed of silicone reinforced with a polymeric mesh, which is bonded to housing 12a by a medical grade epoxy.

First and second sets 60, 70 of opposing features 62, 64 and 72, 74 are independently sealable by pressure exerted by finger F, FIG. 4, in the directions and locations indicated by arrows 80 and 90, respectively. Although they are illustrated as having substantially flat "lands" as abutting surfaces, this is not a limitation of the invention. At the location 80 of finger F as shown in FIG. 4, features 62 and 64 are pressed together to substantially restrict fluid from flowing through inlet 102a and port 16a. Finger F is then moved in a rolling motion, in the direction of arrow 82, to additionally depress the membrane 30a to drive fluid through the port 14a, as illustrated by arrow 56a, to clear the obstruction.

One technique further includes lifting the finger F after the first rolling motion and depressing the membrane with the finger F at location 90 to bring the second set 70 of sealing features 72 and 74 together. Finger F is then moved in a second rolling motion in a second direction, indicated by dashed arrow 92, to additionally depress the membrane 30a to drive fluid in the second direction through the valve inlet 102a and port 16a to clear a second obstruction.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. An implantable valve system comprising:
   a housing with a single dome-shaped resilient membrane defining a reservoir in fluid communication with at least two ports and having a longitudinal axis;
   at least a first set of opposing sealing features disposed on upper and lower surfaces within the housing, the opposing sealing features being disposed in the center region of the reservoir;
   the single dome-shaped membrane capable of being depressed by a human finger to bring the sealing features together to substantially restrict fluid from passing through at least one of one of the ports and to divide the reservoir into a first pumping chamber and a second pumping chamber;
   the single dome-shaped membrane further capable of being depressed additionally by a rolling motion of the finger to drive fluid through the other of the ports; and
   wherein one of the sealing features includes a detent and the other of the sealing features includes a recess to matingly receive the detent.

2. The system of claim 1 wherein the first set of opposing sealing features is disposed transverse to the longitudinal axis of the housing.

3. The system of claim 1 wherein the first set of opposing sealing features extends substantially perpendicularly across the reservoir to establish first and second pumping chambers when the sealing features are brought together.

4. The system of claim 1 in which the housing further includes a floor portion which defines one of the sealing features.

5. A method for clearing an obstruction in a catheter implanted in a patient, comprising:
   locating a valve system implanted sub-dermally in the patient, the valve system having a housing with a single dome-shaped resilient membrane defining a reservoir in fluid communication with at least two ports and having at least a first set of opposing sealing features disposed on upper and lower surfaces within the housing, the opposing sealing features being disposed in the center region of the reservoir;
   depressing the single dome-shaped membrane with one finger to bring the sealing features together to substantially restrict fluid from passing through at least one of one of the ports and to divide the reservoir into a first pumping chamber and a second pumping chamber; and
   moving the finger in a rolling motion to additionally depress the single dome-shaped membrane to drive fluid through the other of the ports to clear the obstruction.

6. A method for clearing obstructions in at least two implanted catheters, comprising:
   locating a valve system implanted sub-dermally in the patient, the valve system having a housing with a single dome-shaped resilient membrane defining a reservoir in fluid communication with at least two ports and having at least a first set of opposing sealing features disposed on upper and lower surfaces within the housing, the opposing sealing features being disposed in the center region of the reservoir;
   depressing the single dome-shaped membrane with one finger to bring the first set of sealing features together to substantially restrict fluid from passing through at least one of one of the ports and to divide the reservoir into a first pumping chamber and a second pumping chamber;
   moving the finger in a first rolling motion in a first direction to additionally depress the single dome-shaped membrane to drive fluid in the first direction through the other of the ports to clear a first obstruction; and
   moving the finger in a second rolling motion in a second direction to additionally depress the single dome-shaped membrane to drive fluid in the second direction through the one of the ports to clear a second obstruction.

\* \* \* \* \*